United States Patent [19]
Kao et al.

[11] Patent Number: 5,266,281
[45] Date of Patent: Nov. 30, 1993

[54] CATALYTIC REACTOR

[75] Inventors: Richard L. Kao, Naperville; Sarabjit S. Randhava; Surjit S. Randhava, both of Evanston; Shaw-Yaw Kang, Chicago, all of Ill.

[73] Assignee: Xytel Technologies Partnership, Mount Prospect, Ill.

[21] Appl. No.: 780,246

[22] Filed: Oct. 22, 1991

Related U.S. Application Data

[63] Continuation-in-part of Ser. No. 409,417, Sep. 16, 1989.

[51] Int. Cl.$^5$ .............................................. B01J 8/06
[52] U.S. Cl. .................................. 422/197; 422/200; 422/201; 422/211; 422/220
[58] Field of Search ............... 422/197, 200, 201, 211, 422/220, 232

[56] References Cited

U.S. PATENT DOCUMENTS

| | | | |
|---|---|---|---|
| 2,029,604 | 2/1936 | Baker et al. | 422/197 X |
| 3,334,971 | 8/1967 | James et al. | 422/197 |
| 3,501,516 | 3/1970 | Parrish | 260/449.5 |
| 3,607,125 | 9/1971 | Kydd | 422/197 |
| 3,962,300 | 6/1976 | Hiller et al. | 260/449.5 |
| 3,993,457 | 11/1976 | Cahn et al. | 260/449 X |
| 4,013,454 | 3/1977 | Jordan | 75/41 |
| 4,048,250 | 9/1977 | Garwood et al. | 260/450 X |
| 4,122,110 | 10/1978 | Sugier et al. | 260/449.5 |
| 4,348,487 | 9/1982 | Goldstein et al. | 518/704 |
| 4,559,207 | 12/1985 | Hiller et al. | 422/197 |
| 4,714,593 | 12/1987 | Naito et al. | 422/197 |

FOREIGN PATENT DOCUMENTS

| | | |
|---|---|---|
| 1159035 | 7/1969 | United Kingdom . |
| 2142331 | 1/1985 | United Kingdom . |

OTHER PUBLICATIONS

Takase et al.-Chemical Abstracts, vol. 104, 1986, 7462b; Mitsubishi (MGC/MHI) Methanol Process, Chem. Econ. Eng. Rev., 17(5), 24–30 (1985).

Monnier, J. R., Apai, G., and Hanrahan, M. J., "Effect of $CO_2$ on the Conversion of $H_2/CO$ to Methanol over Copper-Chromia Catalysts", Journal of Catalysis, 88, pp. 523–525 (1984).

Monnier, J., and Apai, G., "Effect of Oxidation States on the Syngas Activity of Transition Metal Oxide Catalysts", American Chemical Society, 191st National Meeting, Apr. 13–18, 1986.

Primary Examiner—Robert J. Warden
Assistant Examiner—Amalia L. Santiago
Attorney, Agent, or Firm—Speckman, Pauley & Fejer

[57] ABSTRACT

An improved double tube reactor having a plurality of inner and outer tube assemblies each of the assemblies having a reaction annular volume between the inner tube and outer tube and a closed center plug within the inner tube forming an annular thermal exchange volume between the center plug and the inner tube to obtain desired temperature control of exothermic and endothermic catalytic chemical reactions. In one embodiment of the invention, the improved double tube reactor is used in a process for production of high purity methanol from process gas produced by steam reforming hydrocarbon feedstocks in a tube type reformer followed by removing substantially all $CO_2$ and $H_2O$ from the process gas, adjusting the $H_2/CO$ molar ratio to about 2 when necessary, and feeding the adjusted process gas to a methanol synthesis reactor contacting a methanol forming catalyst not requiring $CO_2$ activation at about 200° to about 300° C. to produce product gas comprising methanol, and recovering liquid methanol having purity greater than about 99.85% pure by cooling the product gas to a temperature below the boiling point of methanol and separating the liquid methanol from gaseous components of the product gas. In a preferred embodiment, process gas of $H_2/CO$ molar ratio of about 2.0 to about 2.5 is passed through an annular thermal exchange volume between a center plug and an inner tube followed by passing the gas in contact with a catalyst in a catalyst bed between the inner tube and an outer tube of a double tube reactor assembly promoting the direct reaction of $H_2$ and CO to product methanol.

6 Claims, 4 Drawing Sheets

CATALYTIC REACTOR

CROSS REFERENCE TO RELATED APPLICATION

This application is a continuation-in-part application of Ser. No. 07/409,417 filed Sep. 16, 1989.

BACKGROUND OF THE INVENTION

1. Field of the Invention

This invention relates to an improved double tube reactor and process for its use for catalytic chemical reactions, such as for production of high purity methanol, ammonia, sulfur trioxide, methyl tertiary butyl ether (MTBE) and tertiary amyl methyl ether (TAME) One such use relates to low pressure, low temperature catalytic production of methanol from near stoichiometric ratios of hydrogen and carbon monoxide using the improved double tube reactor.

2. Description of the Relevant Art

Catalytic reactors require heat removal or addition to maintain the desired close control of reactor temperatures necessary for efficient utilization of the catalyst. Various reactor configurations are currently used in attempts to achieve this control. The double tube reactor of the present invention is an inprovement over presently available reactors to maintaining this control. The use of the improved double tube reactor of this invention is described in detail for the exothermic catalytic reaction in the production of high purity methanol from synthesis gases which contain near stoichiometric ratios of hydrogen and carbon monoxide in contact with promoted Cu-Cr oxide catalysts. It is readily apparent to one skilled in the art as to the applicability and manner of use of the improved reactor of this invention for other exothermic catalytic chemical reactions and for endothermic catalytic chemical reactions.

Five general types of methanol synthesis reactors are used for removal of exothermic heat of catalytic reactions. A first type has multiple beds of catalyst in the same vessel and in each catalyst bed the reaction proceeds adiabatically from the inlet to the outlet. Consequently, the reaction mixture temperature rises while the gas mixture is flowing from the inlet to the outlet. Between any two beds of this reactor, the hot reaction mixture may be quenched with a portion of the cold unreacted feed, resulting in low heat recovery and low one-pass conversion. A second type has multiple catalyst beds similar to the first type, however, the inlet temperature of each successive bed is controlled independently by an external waste heat boiler in order to improve the heat recovery and conversion. A third type has a bundle of water tube boilers installed within the catalyst bed to recover the heat of the exothermic catalytic reaction. The heat exchange surface per unit volume of catalyst for this type of reactors is generally small and the heat recovery is reduced accordingly. A fourth type is exemplified by Hiller et al. (U.S. Pat. No. 4,559,207) which teaches the use of catalyst-filled tubes in which the reaction is conducted. These tubes, contained in an outer shell, are externally cooled by boiler water under pressure. The heat of the catalytic reaction is recovered by the generation of high pressure steam in the shell. A fifth type is exemplified by Takase et al., Mitsubishi (MGC/MHI) Methanol Process, Chem. Econ. Eng. Rev., Vol. 17, No. 5, (No. 188) pgs. 24-30 (1985) and Baumann, Heat Exchange in Exothermic Reactors, Czech. Patent 173,670, Aug. 15, 1978. which teach the use of double tube type methanol synthesis reactor in which the catalyst is packed in the annular space between an inner and outer tube. These tubes are cooled externally by boiler water and internally by unreacted feed gas. Thus, a preheater for the feed gas is no longer needed for this type reactor and high pressure steam is generated in the volume between the tubes and outer shell. All of the aforementioned conventional types of catalytic reactors tend to have excessive temperatures in the catalyst beds which injures the catalyst and reduces the catalytic activity.

A number of prior processes have been used for the production of methanol. Until a high pressure/high temperature methanol synthesis technology was developed by BASF in Germany in 1923, distillation of wood was the only commercially significant method to produce methanol. The high pressure/high temperature technology employed a synthetic route using pressurized gas mixtures of $H_2$, CO, $CO_2$ and $CH_4$ in the presence of Zn-Cr based catalysts. The pressurized gas mixtures for methanol synthesis were derived from mixing steam with gaseous, liquid or solid hydrocarbon feedstocks, and preheating to 425° to 550° C. before feeding to a reformer. Very high pressures, typically 300 to 350 atmospheres, were applied in order to obtain a reasonable conversion at the high operating temperatures of the Zn-Cr based catalysts (320° to 380° C.) where the methanol synthesis equilibrium constraints are poor.

In the 1960's, highly active and durable copper-zinc oxide based catalysts were developed for methanol synthesis. These catalysts were so active that the methanol synthesis process could operate at much lower temperatures, 200° to 300° C., than the prior processes and permitted the use of lower operating pressures, 50 to 150 atmospheres. By the late 1970's, most of the methanol synthesis plants in the United States used low pressure technology due to the advantages of lower compression costs, reduced byproduct formation, longer catalyst life, and lower capital costs. The major differences among these low pressure methanol synthesis processes were in the methanol reactor designs used to remove the heat generated by the highly exothermic methanol synthesis reaction and the reformer configurations: one-stage or two-stage reforming. All of the modern low pressure technologies have required a large compressor to bring the process gas to the methanol reactor operating pressure and a step to remove the compressor oil before the methanol synthesis loop. Also, the raw methanol produced from these processes contained approximately 25 mole % water and impurities such as dimethyl ether and higher alcohols. Therefore, a methanol purification step of stripping columns, distillation columns, and the like was needed in order to achieve the required methanol purity.

Several United States patents teach the reaction of $H_2$ plus CO to form methanol U.S. Pat. No. 4,122,110 teaches the reaction of $H_2$ and CO in the presence of a catalyst having at least four metallic components to form linear saturated primary alcohols, the selectivity of $C_2$ or more often being higher than 70% by weight. Several patents teach removal of $CO_2$ from process gas obtained from a hydrocarbon/steam reforming process prior to reaction of $H_2$ and CO in a methanol forming reactor: British patent 1,159,035 teaching $CO_2$ maybe removed completely from the synthesis gas, but part of the removed $CO_2$ is added to the feed to the methanol reactor using a catalyst containing CuO and ZnO and at least one other difficultly reducible Group II to IV metal oxide; U.S. Pat. No. 4,348,487 teaching production of methanol by catalytic coal gasification wherein $CO_2$ is removed from the process gas and then reintroduced back into the methanol synthesis zone feed in order to activate the methanol synthesis catalyst; U.S. Pat. No. 3,962,300 teaching a process for producing methanol using a partial oxidation treatment followed by methanol formation by contacting with a copper-containing catalyst which is indirectly cooled with water boiling under superatmospheric pressure resulting in the production of high pressure steam which is expanded by generating power to produce compression energy for the gases to be compressed in the process, thereby recognizing the problem of compression energy in the methanol production process; and U.S. Pat. No. 4,013,454 teaching partial removal of $CO_2$ in a simultaneous production of methanol or ammonia and again recognizing the problem of $CO_2$ and compression energy in the methanol synthesis process.

A number of patents relating to methanol synthesis recognize that $CO_2$ and $H_2O$ are in the product methanol and must be removed by downstream processes to obtain high purity methanol: U.S. Pat. Nos. 3,501,516; 3,993,457; 4,048,250; and United Kingdom patent application 2142331A.

The use of $Cu-Cr_2O_3$ as a selective catalyst for methanol production without the requirement of $CO_2$ for catalyst activity promotion has been recognized in Monnier, J. R., Apai, G., and Hanrahan, M. J., "Effect of $CO_2$ on the Conversion of $H_2/CO$ to Methanol over Copper-Chromia Catalysts", Journal of Catalysis, 88, pg. 523–525 (1984). The characterization and catalytic activity for methanol formation using promoted Cu-Cr oxide catalysts is taught by J. Monnier and G. Apai, "Effect of Oxidation States on the Syngas Activity of Transition Metal Oxide Catalysts", American Chemical Society, 191st National Meeting, Apr. 13–18, 1986.

SUMMARY OF THE INVENTION

This invention relates to an improved double tube catalytic reactor having a closed center plug within the inner tube to form an annular thermal exchange volume between the center plug and the inner tube for additional thermal exchange. The catalytic reactor of this invention provides much better temperature control of exothermic and endothermic catalytic reactions, as compared with the five types of conventional reactors described above. The improved double tube catalytic reactor of this invention has a plurality of inner tube and outer tube assemblies, each of which assemblies have an annular catalyst bed which functions as a reaction volume between the inner tube and the outer tube and a closed center plug within the inner tube forming an annular thermal exchange volume between the center plug and the inner tube which is capable of thermal transfer. It is preferred that the center plug have a diameter at least 70%, and preferably 80% the inner diameter of the inner tube. It is also preferred that the end of the center plug facing toward the entry of the inner tube be rounded or pointed to facilitate gas flow. This reactor design features high one-pass conversion and high thermal transport.

The improved reactor of this invention is suitable for use in any exothermic or endothermic catalytic chemical reaction. The improved reactor of this invention is particularly important in temperature control of highly exothermic catalytic chemical reactions, such as catalytic production of methanol from near stoichiometric ratios of hydrogen and carbon monoxide over alkali and alkaline earth promoted copper-chromia catalysts; production of ammonia from synthesis gas using an iron oxide catalyst; or production of methyl tertiary butyl ether from isobutylene and methanol over large pore sulfonic resin catalyst.

This invention also relates to low pressure, low temperature catalytic production of methanol from near stoichiometric ratios of hydrogen and carbon monoxide. The process may use hydrocarbon feedstock for steam reforming in a reformer furnace using a pressurized burner to provide higher reformer temperatures. Burner pressure is maintained at about 100 to about 300 psi to result in reformer reaction temperature of about 850° to about 1010° C. to form process gas comprising principally $H_2$, CO, $CH_4$, $CO_2$ and $H_2O$. Higher reforming temperatures produce less methane which reduces the gas volume in the front end of the process and lowers the purge gas rate from the methanol synthesis loop. This allows the application of higher pressure in the reformer tube and makes possible great reduction and elimination of the conventional costly process gas compressor prior to methanol synthesis. The process gas produced by reforming of hydrocarbon feedstock is cooled followed by $CO_2$ and $H_2O$ removal. The $CO_2$ content of the process gas is reduced to less than about 500 ppm $CO_2$ and the $H_2O$ content to less than about 50 ppm $H_2O$. Recovered $CO_2$ is recycled to the reformer and will decrease the $H_2/CO$ molar ratio in the process gas from natural gas feedstock from about 5 to about 3 when a steam/C molar ratio of about 3 is used in the feedstock. This process provides very high carbon utilization. The $H_2/CO$ molar ratio is adjusted to about 2 and slightly greater, preferably about 2.0 to about 2.5, the desired stoichiometric ratio for feed to a methanol synthesis reactor. The methanol synthesis reactor uses a methanol forming catalyst not requiring $CO_2$ activation. Preferred catalysts include alkali and alkaline earth promoted copper-chromia catalysts. Since the catalyst does not require $CO_2$ activation, the absence of $CO_2$ permits reduction and elimination of costly methanol purification, such as strippers and distillation columns. According to this invention, the reacted gas flows to a cooler/condenser and separator. The liquid product from the separator passes through a second separator where the pressure is reduced to release the dissolved gases for reformer fuel. The liquid methanol produced will have 99.85% plus purity. A small portion of the gas released in the first separator is purged in order to maintain a suitable level of inert ($CH_4$) gas in the synthesis loop. The major portion of this gas is mixed with the make-up synthesis gas and recycled to the inlet of the methanol reactor.

In one preferred embodiment, the process of this invention passes process gas comprising $H_2$ and CO in molar ratio $H_2/CO$ of about 2.0 to about 2.5 in a single pass fashion through an annular thermal exchange volume between a center plug and an inner tube of a double tube methanol synthesis reactor followed by passing the heated gas through an annular catalyst bed between the inner tube and the outer tube of the double tube reactor in contact with a catalyst for promotion of reaction of the $H_2$ and CO to product comprising principally methanol.

It is an object of this invention to provide an improved catalytic reactor which results in more favorable temperature profiles for the desired catalytic chemical reaction and steadier and more reliable operation than prior catalytic reactors.

Another object is to provide a reactor for higher heat removal from or heat addition to exothermic or endothermic catalytic chemical reactions, respectively, than prior catalytic reactors.

Yet another object of this invention is to provide a methanol synthesis reactor design which results in more favorable temperature profiles for methanol formation and steadier and more reliable operation.

It is an object of this invention to provide a process and apparatus for production of methanol providing significant reduction of energy consumption and capital investment.

It is another object of this invention to provide high conversion to methanol without the need of a process gas compressor.

It is yet another object of this invention to provide a process for methanol production wherein removal of $CO_2$ and $H_2O$ from the methanol synthesis reactor feed stream eliminates the need for methanol purification, the methanol synthesis reactor providing product gas from which liquid methanol having purity greater than about 99.85% pure may be recovered solely by water cooling the product gas to a temperature below the boiling point of methanol and separating the liquid methanol from gaseous components.

BRIEF DESCRIPTION OF THE DRAWING

The above and other objects and advantages of this invention will become apparent as this description proceeds taken in conjunction with the drawing wherein.

DESCRIPTION OF PREFERRED EMBODIMENTS

Figure 1:
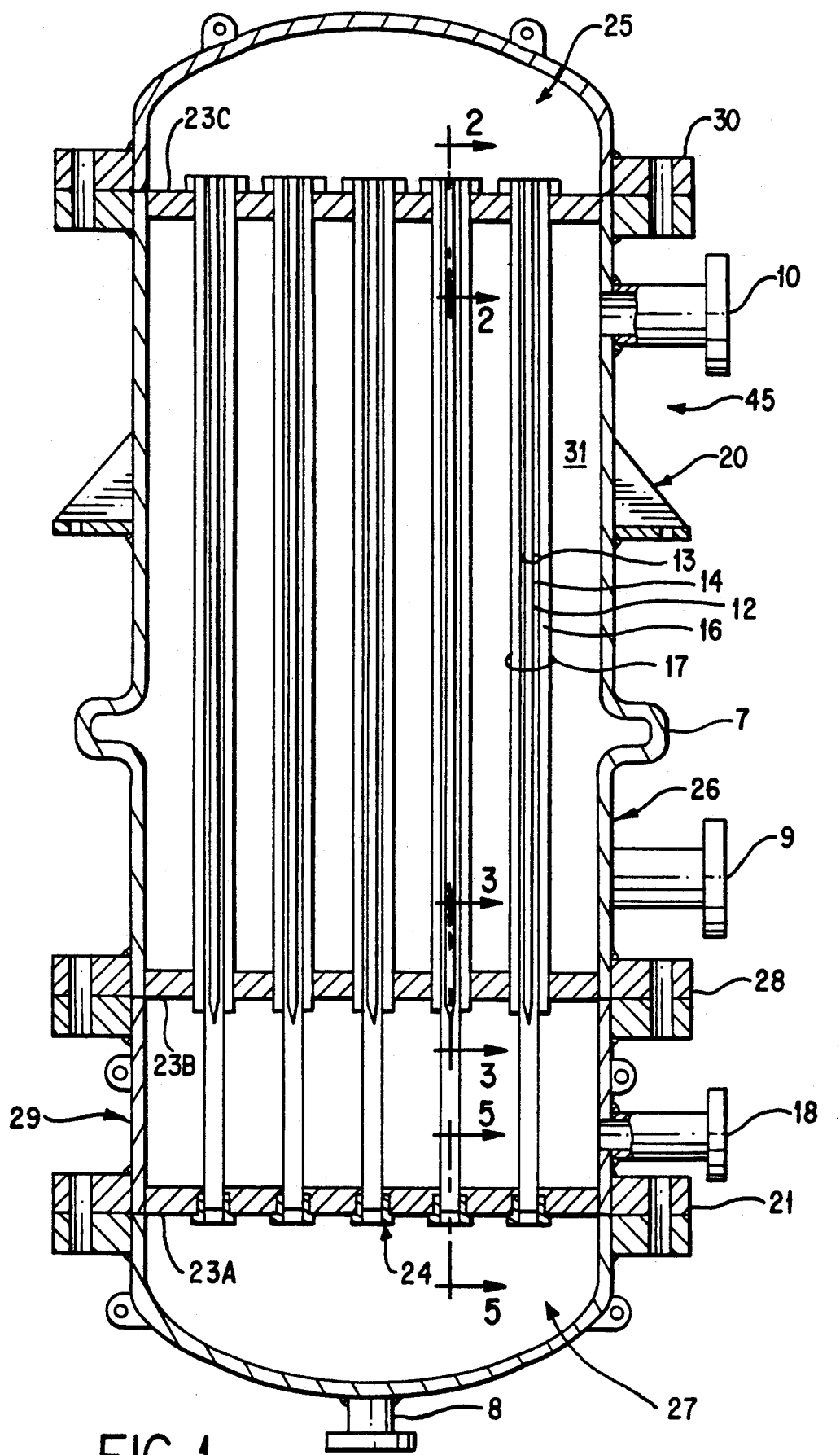
FIG. 1 is a side cross-sectional view of a catalytic reactor according to this invention.
Figure 3:
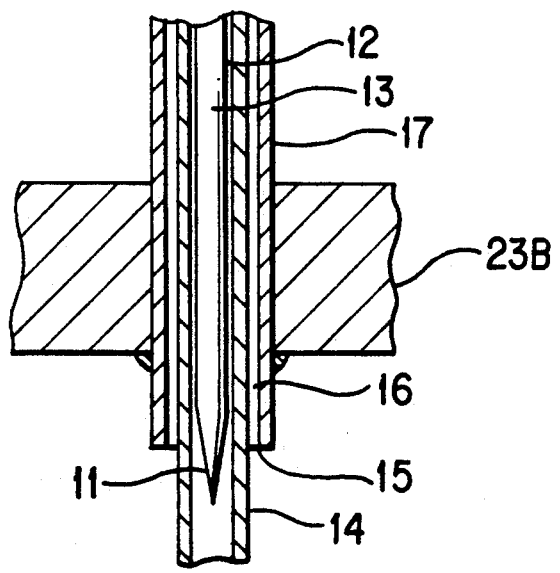
FIG. 3 is an enlarged sectional view of the section shown as 3—3 in FIG. 1.
Figure 4:
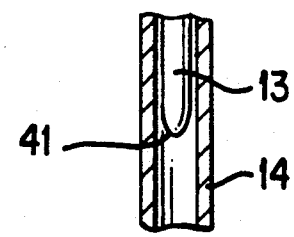
FIG. 4 is an enlarged view of another embodiment of the end of a closed center plug.
Figure 7:
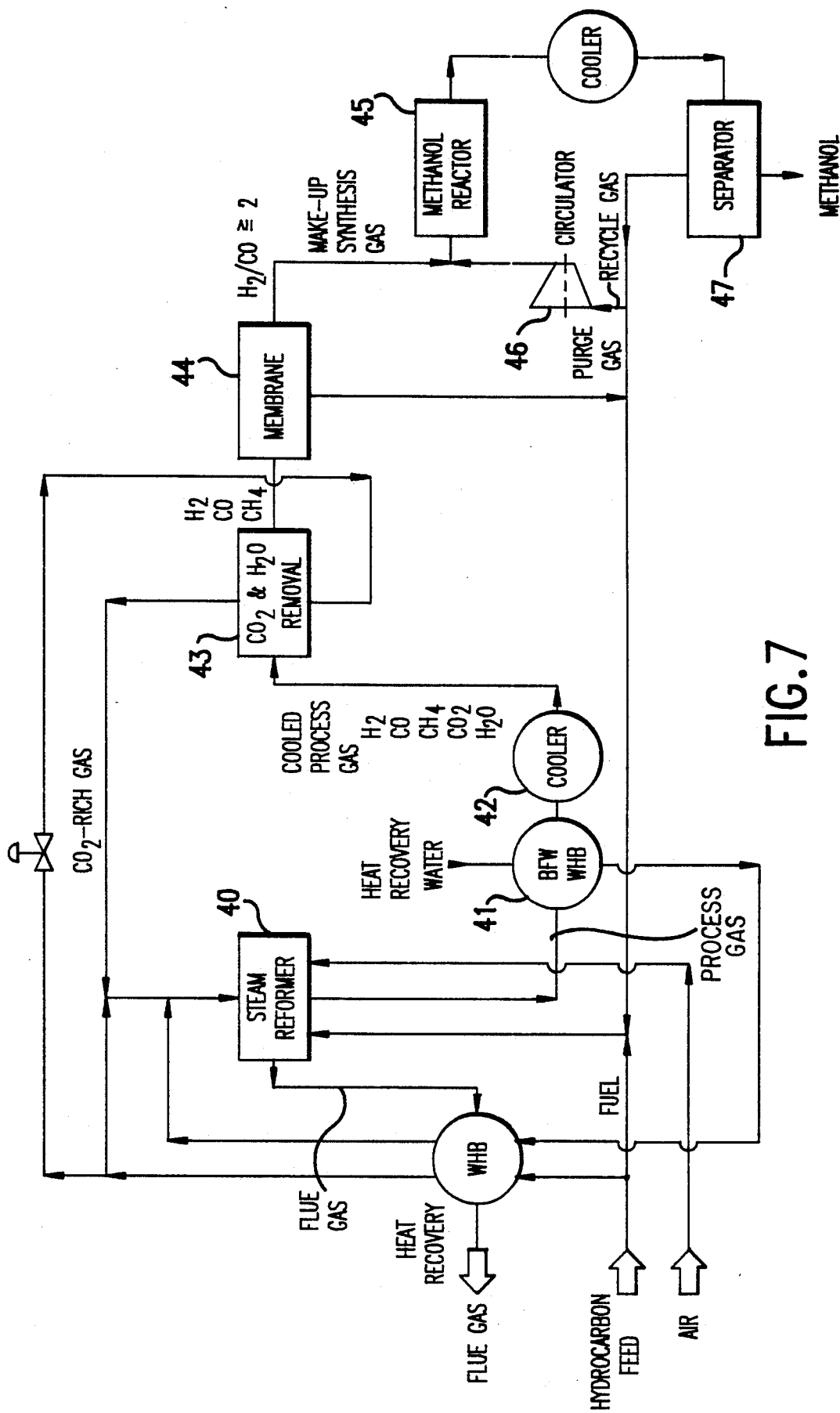
FIG. 7 is a simplified schematic process flow sheet of the methanol synthesis process of this invention.

One suitable catalytic reactor 45 for the process, as shown in FIG. 7, is shown in FIG. 1. The feed gas to the catalytic reactor enters through inlet conduit 8 in bottom dome 27 of the reactor to enter annular thermal exchange volumes 12 between center plugs 13 and inner tubes 14. This may be best seen in FIG. 3 showing center plug 13 with pointed end 11 facing the inlet end of inner tube 14. Another embodiment is shown in FIG. 4 showing center plug 13 with curved end 41 facing the inlet end of inner tube 14. Any end shape to promote desired gas flow may be used. Between inner tube 14 and outer tube 17 is annular catalyst bed 16. Annular thermal exchange volume 12 between center plug 13 and inner tube 14 and the space outside the outer tube 17 provide superior heat transfer for the catalyst bed 16 and result in good temperature profiles in the catalyst bed 16 for steady-state operation. The process feed gas is preheated by passage through annular thermal exchange volumes 12 by reaction heat generated in catalyst beds in annular catalyst volumes 16. The preheated process gas enters the volume of upper dome 25 and then passes through annular catalyst beds 16 flowing downward between inner tubes 14 and outer tubes 17 exiting at product gas outlet 18. It is preferred that the center plugs 13 have a diameter at least 70%, and more preferably at least 80%, the inner diameter of the inner tubes 14. Annular catalyst beds 16 are cooled externally by pressurized boiler water entering at inlet 9 and exiting at outlet 10 and internally by process gas passing through the annular thermal exchange volumes 12 between inner tubes 14 and center plugs 13. This provides both radial and vertical temperature profiles in the catalyst beds, a lower temperature at the bottom of the catalyst bed with gradual increase in temperature toward the top which is favorable in terms of the catalytic exothermic chemical reaction. The catalytic reactor of this invention provides favorable temperature control, as compared with conventional catalytic reactors described above. While specifically described with respect to exothermic catalytic reactions, the manner of use and applicability to endothermic catalytic reactions is readily apparent to one skilled in the art.

Figure 2:
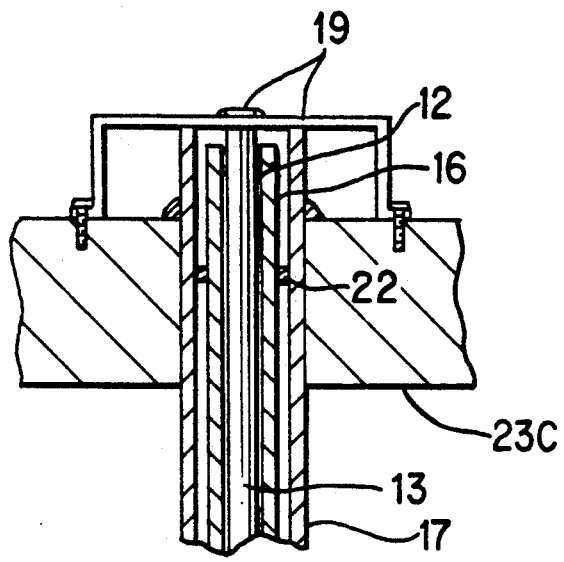
FIG. 2 is an enlarged sectional view of the section shown as 2—2 in FIG. 1.
Figure 5:
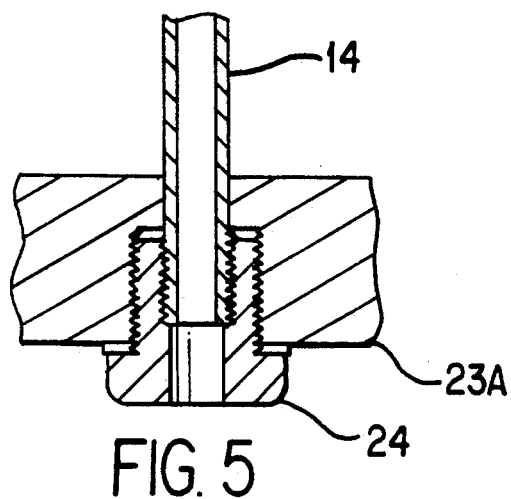
FIG. 5 is an enlarged sectional view of the section shown as 5—5 in FIG. 1.
Figure 6:
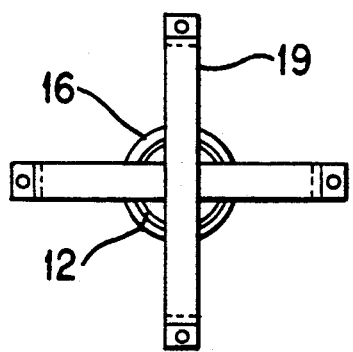
FIG. 6 is a top view of the portion shown in FIG. 2.

In the embodiment shown, the reactor vessel of this invention may be installed vertically, four lug supports 20 holding the entire weight of the vessel. The reactor shown in FIG. 1 provides for simple charge and discharge of the catalyst. Lower dome 27 may be removed from vessel 26 by removing bolts from bottom flange 21, dropping lower dome 27. Lower tube plate 23A is now exposed, and as best seen in FIG. 5, end plugs 24 may be unscrewed from the face of lower tube plate 23A and inner tubes 14 pulled from vessel 26. In a similar manner, lower vessel body 29 may be removed from vessel 26 by removing bolts of flange 28 exposing the open ends of outer tubes 17 from which the catalysts may be readily discharged by removing the catalyst supports 15. As best seen in FIGS. 2 and 3, outer tube 17 is fixed to central tube plate 23B and upper tube plate 23C. As best seen in FIG. 2, center plug 13 is fixed to upper tube plate 23C by bracket 19 which provides opening to annular thermal exchange volume 12 and annular catalyst bed volume 16. To reassemble, reactor lower vessel body 29 is rebolted to vessel 26 by flange 28. Using center plugs 13 as guides, inner tubes 14 are inserted back into outer tubes 17 and end plugs 24 are reinstalled in lower tube plate 23A. Once tightened, inner tubes 14 are supported and fixed by lower tube plate 23A and kept centered by spacers 22. Lower dome 27 is refastened to vessel 26 by bolting through flange 21. Upper dome 25 may be removed by removing the bolts through flange 30 exposing the upper ends of annular catalyst bed volume 16 between inner tubes 14 and outer tubes 17. New catalyst can be easily charged into the annular catalyst bed space 16 and the upper dome 25 replaced.

Due to unequal thermal expansion of the tube bundles and reactor vessel 26, bellow expansion joint 7 is provided so that neither vessel 26 nor the tubes are stretched or compressed.

The reactor vessel and components of the catalytic reactor may be constructed of any suitable materials known to one skilled in the art and as suitable for temperatures and pressures involved.

Referring to FIG. 7, the overall process for methanol production may be divided into four principal sections: reforming; process gas $CO_2$ and $H_2O$ removal; $H_2/CO$ stoichiometry adjustment; and methanol synthesis loop.

We have found that operation of the catalytic reactor in the methanol synthesis process of this invention at temperatures of about 200° to about 300° C. and pressures of about 400 to about 800 psi provide liquid methanol having purity greater than about 99.85% pure by cooling the product gas to a temperature below the boiling point of methanol and separating the liquid methanol from gaseous components of the product gas which may then be recycled.

As shown in FIG. 7, hydrocarbon feed, steam and air are fed to steam reformer 40. One method of overcoming problems of stress-rupture failures of the catalyst tubes due to high temperature/high pressure operation is to use a pressurized burner in the reformer according to this invention, burner pressures suitably maintained at about 100 to 300 psi and preferably about 150 to 200 psi to provide higher reformer reaction temperatures of about 850° to about 1010° C. and preferably about 950° to about 1010° C. For example, a 100 psi increase in burner pressure can increase the temperature of a reformer tube from 954° C. to about 982° C. Reformer tubes which will withstand the additional temperature must be used in the steam reformer 40. Suitable desulfurized hydrocarbon feeds to the steam reformer according to this invention include gaseous, liquid, and solid hydrocarbon feedstocks, and mixtures thereof. For example, natural gas may be used as feedstock, hydrocarbon oils may be used as feedstock, and coal or shale may be used as feedstock, and mixtures of such feedstocks may also be used, as is well known in steam reforming techniques. Operation of the steam reformer of this invention at higher temperatures than conventional steam reformers results in lower methane in the process gas and reduces the methane purge rate from the methanol synthesis loop and also allows the application of higher pressure in the reformer tube. Process gas, comprising principally $H_2$, CO, $CH_4$, $CO_2$ and $H_2O$ passes through waste heat boiler 41 where high pressure seam is produced. The remaining heat is utilized to the maximum extent as a BFW preheat 41. The final cooling and condensation of extra steam content in the process gas are done by air and water thermal exchange in cooler 42, cooling the process gas to about 43° C. While the process of this invention preferably utilizes process gas obtained by steam reforming of hydrocarbon feedstocks, similar process gas produced by other processes, such as partial oxidation, may also be used.

Carbon dioxide and $H_2O$ removal from the cooled process gas may be achieved by various $CO_2$ and $H_2O$ removal means 43. One desirable method is by pressure swing absorption using molecular sieves. The pressure swing absorption product gas would contain less than about 10 ppm $H_2O$ and less than about 500 ppm, preferably less than about 100 ppm, $CO_2$. The pressure swing absorption molecular sieve process is advantageous since it requires virtually no utilities and no operating attention, operates at ambient temperature, fully automated, with no external regenerant gas, and may be shut down and started up quickly with very little attention. The recovered $CO_2$ stream contains about 15% of the feed $H_2$, 30% of the feed CO and 40% of the feed $CH_4$ which may be recycled back to the steam reformer. Another system for $CO_2$ and $H_2O$ removal is to use an inhibited amine system to scrub the $CO_2$ followed by a thermally regenerated molecular sieve gas dryer wherein the cooled process gas enters the bottom of a $CO_2$ absorber and flows up through either packed beds or trays countercurrent to an aqueous solution of alkanolamine, such as monoethanolamine and diethanolamine, wherein $CO_2$ may be removed from the process gas to less than 100 ppm. The $CO_2$-rich spent solution is pumped from the bottom of the absorber to a lean/rich heat exchanger where it is heated to above 100° C. by a hot lean alkanolamine solution. Then the alkanolamine solution is fed to the top of a stripper where the absorbed $CO_2$ is stripped from the descending spent solution by a rinsing hot stream of steam which is generated by a reformer waste heat boiler. The steam and recovered $CO_2$ are recycled to the reformer feed while the regenerated or lean alkanolamine solution flows to the lean/rich heat exchanger before it is pumped to the top of the absorber for completion of the purification cycle. The purified gas passes through a molecular sieve gas dryer to remove the moisture and part of the remaining $CO_2$. The dryer may comprise dual molecular sieve chambers, one of which may be on a process line and one of which may be regenerated by a hot stream of pressurized $CH_4$. The alkanolamine stripping has the advantage of about a 99% recovery of $H_2$ and CO while producing a product gas with less than about 100 ppm $CO_2$. However, the alkanolamine stripping process has some disadvantages when compared to the pressure swing absorption molecular sieve process in that it requires more operating attention and has heat input and cooling water requirements in addition to the molecular sieve gas dryer. Another process for removal of $CO_2$ and $H_2O$ is the use of physical solvents such as the SELEXOL solvent removal system which uses an absorber for the process gas $CO_2$ and $H_2O$ removal simultaneously and a stripper for regeneration of the spent solution first by stripping, followed by flashing. The advantage of this system is that $CO_2$ can be recovered by stripping with a hot stream of pressurized $CH_4$ or steam, thus eliminating the need for $CO_2$ recycle compressor. A major disadvantage of this system is that external cooling is required. Any of the above $CO_2$ and $H_2O$ removal systems may be used in the process of this invention and the choice is dependent upon optimizing the design for individual applications, depending upon available utilities.

$H_2$/CO stoichiometry adjustment may be effected by any suitable adjustment means shown in FIG. 7 as 44, such as a membrane unit. It is desired that the feed gas to methanol synthesis reactor 45 has an $H_2$/CO molar ratio of about 2.0 to about 2.5, preferably about 2.0 to about 2.2. The molar ratio of $H_2$ to CO in the process gas depends upon the hydrocarbon feedstock used. For example, when naphtha is used as the reformer feedstock the $H_2$/CO molar ratio will be 2, while when natural gas is used the ratio will be about 5. When natural gas and recovered $CO_2$ and $H_2O$ are used as reformer feedstock, the $H_2$/CO ratio is about 3. As excess $H_2$ accumulates in the methanol synthesis loop, a high purge gas rate is required, the purge stream taking along whatever amount of CO corresponds to the composition in the recycle. It is more economical to remove the excess $H_2$ by a membrane unit before the makeup synthesis gas enters the methanol synthesis loop. Thus a lower recycle ratio is required to accommodate the trace amount of inerts, which results in smaller sized equipment and lower power consumption for the recycle circulator 46. In prior art methanol synthesis reactors the following reactions have occurred:

(1) $CO + 2H_2 \longrightarrow CH_3OH$ (2) $CO_2 + 3H_2 \longrightarrow CH_3OH + H_2O$ (3) $2CO + 4H_2 \longrightarrow CH_3OCH_3 + H_2O$ (4) $CO + 3H_2 \longrightarrow CH_4 + H_2O$ (5) $nCO + 2nH_2 \longrightarrow C_nH_{(2n+1)}OH + (n-1)H_2O; n > 1$ According to the process of this invention, when $CO_2$ is not present in the methanol synthesis reactor feed, reaction 2, a major source of water production, does not occur. In the process of this invention using highly methanol selective alkali and alkaline earth promoted copper-chromia catalysts, the side reaction of equation (4) is not present. Since the catalysts used in this invention are low pressure catalysts, the amount of impurities, such as dimethyl ether, higher alcohols, and carbonyl compounds in the methanol are also reduced significantly. Equations (3) and (5) represent side reactions for low pressure methanol processes and we have found the total amount of impurities in the liquid methanol produced in the synthesis loop is normally below about 1000 ppm, therefore, producing a very high purity methanol without the conventional requirement of methanol purification by stripper and distillation columns. The reaction of equation (1) is clearly the predominant reaction of the process of this invention, not producing $H_2O$. As shown in FIG. 7, the $CO_2$ and $H_2O$ free process gas having an $H_2/CO$ molar ratio of 2 or slightly greater is mixed with recycle gas from circulator 46 before entering methanol synthesis reactor 45.

While described with respect to a specific process for production of high purity methanol it is readily apparent that the apparatus and process of this invention is applicable to any process for conduct of a catalytic exothermic or endothermic chemical reaction in double tube reactors comprising a plurality of inner and outer tube assemblies having a reaction annular volume between the inner tube and the outer tube, the improvement of this invention comprising passing reactant gas through an annular thermal exchange volume between a closed center plug and the inner tube which is capable of thermal transfer followed by passing the gas in contact with a catalyst for promotion of the desired catalytic chemical reaction in an annular catalyst bed in the reaction annular volume.

While in the foregoing specification this invention has been described in relation to certain preferred embodiments thereof, and many details have been set forth for purpose of illustration. It will be apparent to those skilled in the art that the invention is susceptible to additional embodiments and that certain of the details described herein can be varied considerably without departing from the basic principles of the invention.

We claim:

1. In a double tube catalytic reactor comprising a plurality of inner tube-and-outer tube assemblies within a reactor vessel, each of said assemblies having a reaction annular volume containing catalyst between the inner tube and the outer tube, the improvement comprising;

a liquid source means feeding a liquid into said reactor vessel and around said plurality of assemblies, a center plug centrally and coaxially located within said inner tube forming an annular thermal exchange volume between said center plug and said inner tube which is capable of thermal transfer, and said outer tube which is capable of thermal transfer in communication with said flowing liquid within said reactor vessel, the combination of thermal transfer between said catalyst and said annular thermal exchange volume on one side of the catalyst, and with said flowing liquid on the opposite said of the catalyst providing control of both radial and axial temperature profiles in said catalyst during exothermic or endothermic chemical reactions.

2. An improved double tube reactor according to claim 1 wherein said center plug has a diameter at least 70 percent the inner diameter of said inner tube.

3. An improved double tube reactor according to claim 1 wherein said center plug has a diameter at least 80 percent the inner diameter of said inner tube.

4. An improved double tube reactor according to claim 1 wherein said center plug has a pointed end shape facing toward an end of said inner tube for inlet of process gas.

5. An improved double tube reactor according to claim 1 wherein said center plug has a rounded end shape facing toward an end of said inner tube for inlet of process gas.

6. An improved double tube reactor according to claim 1 wherein said center plug has an end facing toward an end of said inner tube for inlet of process gas shaped to facilitate the flow of gas into said annular thermal exchange volume.

* * * * *